(12) United States Patent
Ostermaier

(10) Patent No.: US 7,678,906 B2
(45) Date of Patent: *Mar. 16, 2010

(54) PROCESS FOR MAKING TRIPHENYLBORON-PYRIDINE COMPOUND

(75) Inventor: John J. Ostermaier, Orange, TX (US)

(73) Assignee: Invista North America S.A.R.L., Wilmington, DE (US)

( * ) Notice: Subject to any disclaimer, the term of this patent is extended or adjusted under 35 U.S.C. 154(b) by 142 days.

This patent is subject to a terminal disclaimer.

(21) Appl. No.: 12/027,432

(22) Filed: Feb. 7, 2008

(65) Prior Publication Data

US 2008/0154039 A1 Jun. 26, 2008

Related U.S. Application Data

(63) Continuation-in-part of application No. 11/473,907, filed on Jun. 23, 2006, now Pat. No. 7,517,985.

(51) Int. Cl.
 *C07F 5/02* (2006.01)

(52) U.S. Cl. .................................................. 546/13
(58) Field of Classification Search .................. 546/13
 See application file for complete search history.

(56) References Cited

U.S. PATENT DOCUMENTS

| 3,211,679 A | 10/1965 | Updegraff |
| 7,517,985 B2 * | 4/2009 | Ostermaier et al. ........... 546/13 |

FOREIGN PATENT DOCUMENTS

| JP | 08-311074 | 11/1996 |
| JP | 2003-238572 | * 8/2003 |

* cited by examiner

*Primary Examiner*—Charanjit S Aulakh

(57) ABSTRACT

A process for improving the recovery of solid triphenylboron-pyridine compound (TPBP), while retaining desirable particle characteristics comprises the addition of an acid to neutralize at least a portion of the alkali contained in the aqueous mother liquor. By adjusting the pH of the product slurry to between about 8.5 and about 12, it is possible to increase product recovery by more than 10%, while maintaining desirable particle characteristics.

21 Claims, 2 Drawing Sheets

Figure 1          (for Example 1)
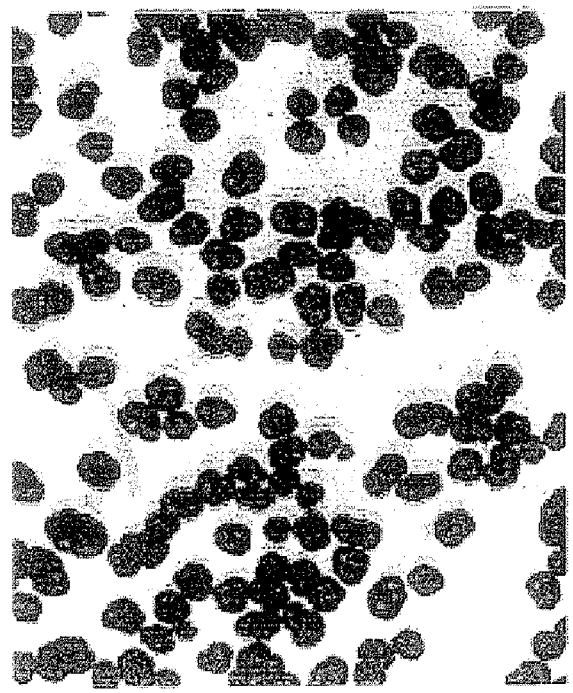
Figure 2          (for Example 2)
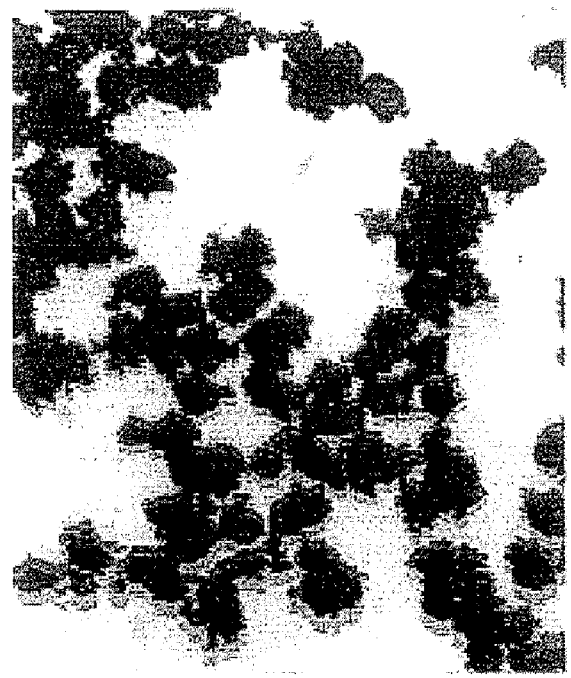

Figure 3 (for Example 3)
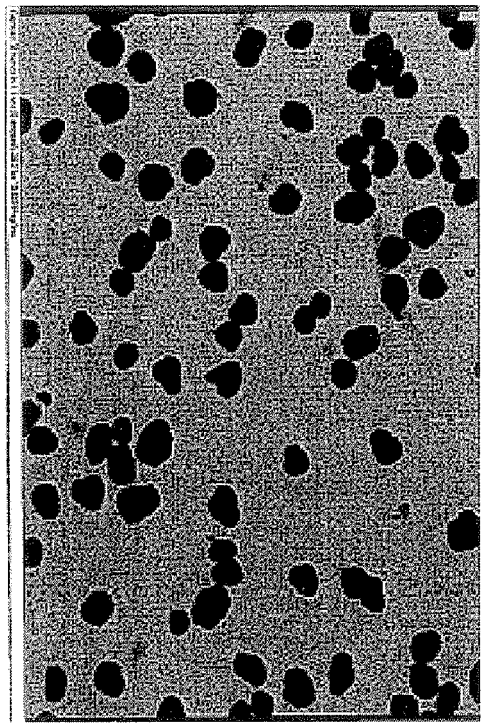
Figure 4 (for Example 4)
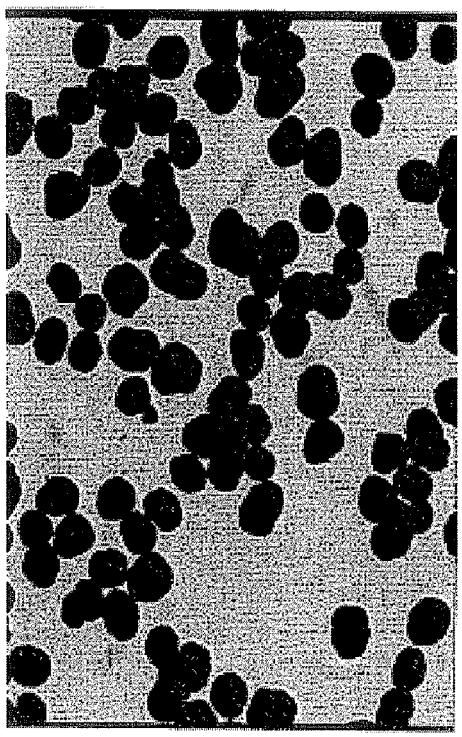

PROCESS FOR MAKING TRIPHENYLBORON-PYRIDINE COMPOUND

CROSS-REFERENCE TO RELATED APPLICATION

This application is a continuation-in-part of U.S. patent application Ser. No. 11/473,907, filed on Jun. 23, 2006, now U.S. Patent Application Publication No. 2007/0299259A1, incorporated herein by reference.

FIELD OF INVENTION

The invention relates to a process for producing triphenyl-boron-amine compounds. The invention particularly relates to a process for producing solid triphenylboron-pyridine compound (TPBP), by the precipitation reaction between pyridine and an aqueous sodium hydroxide or potassium hydroxide adduct of triphenylboron, which will be designated individually or collectively as TBPA throughout this application.

BACKGROUND

Triphenylboron-amine compounds, and triphenylboron-pyridine (TPBP) compounds in particular, are known to be effective biocides and marine anti-fouling agents and are, therefore, commercially important products. See for example U.S. Pat. No. 3,211,679.

One method for making TPBP is by the reaction of TPBA with pyridine in aqueous solution. See JP 08311074 (the "JP 1074 Application") and U.S. patent application Ser. No. 11/473,907 filed Jun. 23, 2006 (the "'907 application"), both incorporated herein by reference. Solid TPBP particles precipitate out when TPBA is reacted with pyridine.

However, after addition of pyridine to the aqueous TPBA, the resulting product slurry contains three moles of alkali (e.g., alkali metal hydroxide) for every mole of TPBP. Since the solubility of TPBP in an aqueous solution increases with increasing concentration of alkali, a considerable amount of the product TPBP is dissolved in the mother liquor.

SUMMARY OF INVENTION

Thus, it is an object of this invention to provide a process that converts at least a portion of the soluble TPBP to a solid product, and thereby increases the recovery of solid TPBP.

In one embodiment, the invention is directed to an improved process for making generally spherical TPBP solid particles which comprises (A) forming (or providing) a product slurry comprising solid TPBP particles in an aqueous mother liquor in a vigorously agitated reaction zone; (B) separately feeding into the vigorously agitated reaction zone (i) a stream comprising pyridine and (ii) a stream comprising a solution of TPBA at such rate that the total concentration of TPBA in the combined feed streams is in the range of from about 1 wt % to about 6 wt %. As a result, additional TPBP is formed, some of which will become suspended as a solid in the aqueous mother liquor and some will be dissolved in the aqueous mother liquor. To the product slurry, which now includes this additional TPBP, is added an acid in a sufficient amount to adjust the pH of the product slurry to a value between about 8.5 to about 12.0. A product stream is removed from the reaction zone at such a rate that the volume of the product slurry in the reaction zone remains substantially constant, and the concentration of solid TPBP in the product slurry is maintained at a value of less than about 8 wt %.

In an alternative embodiment, the invention is directed to an improved process for producing triphenylboron-pyridine (TPBP) which comprises: separately feeding into a vigorously agitated reaction zone (i) a stream comprising pyridine and (ii) a stream comprising a solution of TPBA to form a product slurry. The product slurry comprises some TPBP particles suspended in an aqueous mother liquor and some TPBP dissolved in an aqueous mother liquor. To the product slurry is added a sufficient amount of acid to adjust pH of the product slurry to a value of about 8.5 to about 12.0. Subsequently, a product stream which contains the TPBP particles is removed from the reaction zone.

All embodiments of the invention increase the yield of TPBP. In all embodiments product slurry may also be referred to as a "suspension".

All embodiments of the invention are, therefore, directed to processes for increasing the recovery of TPBP solid when TPBA is reacted with pyridine in an aqueous solution as described in the JP 1074 and the U.S. '907 applications. By adding acid to the product slurry to neutralize the soluble alkali, the amount of alkali in the product slurry is reduced, which subsequently reduces the amount of soluble TPBP, and increases the amount of recoverable solid TPBP.

In all embodiments, the neutralization must be carefully controlled to give a product slurry pH of between about 8.5 and about 12. The addition of insufficient acid produces a product slurry pH above about 12, and reduced recovery. The addition of excess acid produces a product slurry pH less than about 8.5. While the pH less than about 8.5 gives good product recovery, it also causes the particle characteristics to change in an undesirable manner.

BRIEF DESCRIPTION OF THE DRAWINGS

FIG. 1 is a photomicrograph of the product obtained in Example 1.

FIG. 2 is a photomicrograph of the product obtained in Example 2.

FIG. 3 is a photomicrograph of the product obtained in Example 3.

FIG. 4 is a photomicrograph of the product obtained in Example 4.

DETAILED DESCRIPTION OF THE INVENTION

The term "mother liquor" is used herein to describe the aqueous phase in the reaction zone, e.g., a reactor or crystallizer, which includes dissolved TPBP, dissolved alkali (NaOH, also referred to as "caustic", or KOH) and the corresponding dissolved alkali metal chloride salt (sodium chloride or potassium chloride).

In all embodiments, "vigorously agitated reaction zone" may also be referred to herein as a "well mixed reaction zone".

The reaction zone for all embodiments may be any suitable vessel, such as a crystallizer, a reactor or back-mixed precipitating reactor. The separate neutralization vessel, if used, may be any suitable agitated vessel.

In all embodiments, the pyridine-containing stream can be undiluted pyridine or diluted with an aqueous mother liquor or water.

In all embodiments, the acid is a non-oxidizing acid, such as hydrochloric acid, sulfuric acid, phosphoric acid or acetic acid, and a sufficient amount of the acid is added to adjust pH of the product slurry to a value of about 8.5 to about 12.0, such as about 9 to about 12, about 9.5 to about 11, or about 9.5 to about 10.5.

Embodiment With Previously-Formed Product Slurry Of Solid TPBP Particles In Aqueous Mother Liquor In one embodiment of the invention, a solid triphenylboron-pyridine compound (TPBP) is produced by introducing separately and substantially continuously an aqueous solution of pyridine, and a stream of aqueous TPBA into a well mixed reaction zone, e.g., a crystallizer, that includes a product slurry comprising solid TPBP particles in a mother liquor. A stream of the product slurry is removed substantially continuously from the crystallizer to maintain a substantially constant inventory in the crystallizer. The residence time of the product slurry in the crystallizer is greater than about 10 minutes, such as about 30 minutes or about 1 hour. The specific mode of operation of the crystallizer is described in detail in Patent Application Publication No. 2007/0299259A1, and is summarized below.

When operating at optimal conditions, the concentration of alkali in the aqueous mother liquor is 0.5 molar, which corresponds to a pH of 13.7. The product slurry from the crystallizer can be reacted in a separate vessel with any non-oxidizing acid, such as HCl, to neutralize the alkali and reduce the pH of the product slurry. The amount of the acid added should be sufficient to reduce the pH to between about 8.5 and about 12, such as between about 9.5 and about 10.5. The concentration of the acid is not critical, and normally concentrated acid, e.g., concentrated HCl, would be used.

In more detail, in this embodiment, a pyridine-containing stream and a stream of TPBA are fed, e.g., by metering, separately into a reaction zone, such as, a reactor, a crystallizer, or other suitable vessel, that contains a previously formed product slurry of solid TPBP particles in an aqueous mother liquor. The TPBA reacts with pyridine to form solid TPBP particles, i.e., one mole of pyridine and one mole of TPBA react to form one mole of TPBP and one mole of alkali. Some of the formed TPBP is dissolved in the mother liquor, while the remainder is suspended as solid particles in the mother liquor. The product slurry, which now includes the formed TPBP particles, is fed from the crystallizer to an agitated tank where the acid is added to neutralize a portion of the alkali.

The reaction zone is equipped with an agitator for vigorously agitating the suspension during operation of the process. The term "vigorous agitation" is well within the skill in the art and is intended to mean well agitated and continuous mixing of the suspension in the reactor that is designed to insure uniform and generally rapid mixing of the reactant streams as they are introduced into the reactor. During continuous operation of the process, a product stream is withdrawn, e.g., substantially simultaneously withdrawn, from the reaction zone, and the feed flow rates of the pyridine-containing stream, the TPBA stream and the product stream are adjusted so that the volume of product slurry in the reaction zone is maintained at a predetermined generally constant value so that the residence time is at least about 10 minutes, as described below. Maintaining a convenient volume of product slurry in the reaction zone in correspondence with the size of the reactor, the crystallizer or other suitable vessel, and the agitator capability will produce satisfactory results.

Generally spherically shaped TPBP particles having a mean diameter greater than about 20 microns and a Gaussian particle size distribution can be consistently produced on a continuous basis. The TPBP particles are recovered as a filter cake, and the filter cake in the recovery process exhibits improved properties with respect to filtration, washing, and drying when the TPBA content of the combined TPBA stream and pyridine stream is maintained in a range from about 1 wt % to about 6 wt %, such as about 3 wt % to about 5 wt %.

Introduction of the pyridine-containing stream and the TPBA stream and removal of the product stream should be conducted on a continuous basis, however, the process can also be run on an intermittent basis. Solid TPBP can be recovered from the product stream by filtration or by any other convenient solid-liquid separation technique. Typical devices include rotary vacuum filters, centrifugal filters, and pusher centrifuges.

Temperature can have an effect on the characteristics of the TPBP particles formed. Higher temperatures generally favor larger particles, although temperatures above 60° C. have been observed to cause undesirable changes in product morphology. In carrying out the process, the temperature in the reaction zone, i.e., the temperature of the suspension in the reaction zone, should be in the range of from about 20° C. to about 60° C. such as about 35° C. to about 45° C.

The concentration of alkali in the TPBA solution can vary over a range, such as about 0.4 to about 0.6 moles alkali/liter of TPBA solution. The TPBA solution may contain other components, such as alkali metal chloride salt, at a concentration in the range of from about 0.6 to about 0.9 moles alkali metal chloride salt/liter of TPBA solution.

To begin the process, a product slurry of solid TPBP particles may be formed in the reaction vessel by an initial batch-wise precipitation reaction between pyridine and TPBA solution. A product slurry held over from a previous batch-wise or continuous operation of the process may also be used.

The reaction zone for carrying out the process can be a crystallizer with a suitable agitator or other mixing device. The size of the reaction vessel (i.e., reaction zone) is chosen to give a residence time (defined as the volume of the slurry maintained in the vessel divided by the total volumetric feed rate) greater than about 10 minutes, such as about 30 minutes or about 1 hour. Agitation can be provided by an agitator or by a circulation loop or by both means. Reactor vessels, such as crystallizers, will typically be equipped with internal baffles arranged about the periphery of the vessel, and may be equipped with a draft tube. Aside from the addition of the acid and any changes necessitated by it, such as modification of the pH, the specific mode of operation of the crystallizer is described in detail in the '907 application.

In an alternate embodiment at least a portion of the acid or all of the acid may be added within the reaction zone (e.g., crystallizer) provided that desirable product crystal characteristics are maintained.

Embodiment without Previously-Formed Product Slurry of Solid TPBP Particles in Aqueous Mother Liquor In the alternative embodiment of the invention, the TPBP is prepared in a process comprising adding substantially continuously a stream comprising pyridine, and a separate stream comprising an aqueous solution of TPBA to a well mixed reaction zone, e.g., a crystallizer, which does not contain a previously-formed product slurry of solid TPBP particles in aqueous mother liquor. The TPBA solution reacts with pyridine to form solid TPBP particles, i.e., one mole of pyridine and one mole of TPBA react to form one mole of TPBP and one mole of alkali. Some of the formed TPBP is dissolved in the mother liquor, while the remainder is suspended as solid particles in the mother liquor. A stream of the product slurry is removed, e.g., substantially continuously, from the crystallizer to maintain a substantially constant inventory in the crystallizer. The residence time of the product slurry in the crystallizer is greater than about 10 minutes, such as about 30 minutes or about 1 hour. The product slurry from the reaction zone is reacted in a separate vessel (e.g., agitated tank) with a sufficient amount of any non-oxidizing acid, such as HCl, to adjust the pH of the product slurry to a value of about 8.5 to about 12, such as about 9.5 to about 10.5. The concentration of the acid is not critical, and normally concentrated acid, e.g., concentrated HCl, would be used.

The reaction zone is equipped with an agitator for vigorously agitating the product slurry during operation of the process. The term "vigorous agitation" is well within the skill in the art and is intended to mean well agitated and continuous mixing of the product slurry in the reactor that is designed to insure uniform and generally rapid mixing of the reactant streams as they are introduced into the reactor. During continuous operation of the process, a product stream is withdrawn, e.g., substantially simultaneously withdrawn, from the reaction zone, and the feed flow rates of the pyridine-containing stream, the TPBA stream and the product stream are adjusted so that the volume of product slurry in the reaction zone is maintained at a predetermined generally constant value so that the residence time is at least about 10 minutes, as described below. Maintaining a convenient volume of product slurry in the reaction zone in correspondence with the size of the reactor, the crystallizer or other suitable vessel, and the agitator capability will produce satisfactory results.

Generally spherically shaped TPBP particles having a mean diameter greater than about 20 microns and a Gaussian particle size distribution can be consistently produced on a continuous basis. The TPBP particles are recovered as a filter cake.

The introduction of the pyridine-containing stream and the TPBA solution stream and removal of the product stream should be conducted on a continuous basis, however, the process can also be run on an intermittent basis.

Solid TPBP can be recovered from the product stream by filtration or by any other convenient solid-liquid separation technique. Typical devices include rotary vacuum filters, centrifugal filters, and pusher centrifuges.

The reaction is carried out at room temperature or at elevated temperature of about 20 to about 60° C. The total concentration of TPBA in the combined TPBA solution stream and pyridine stream is maintained in a range from about 1 wt % to about 6 wt %, such as about 3 wt % to about 5 wt %.

The concentration of alkali in the TPBA solution can vary over a range, such as about 0.4 to about 0.6 moles alkali/liter of TPBA solution. The TPBA solution may contain other components, such as alkali metal chloride salt, at a concentration in the range of from about 0.6 to about 0.9 moles alkali metal chloride salt/liter of TPBA solution.

The reaction zone for carrying out the process can be a crystallizer with a suitable agitation or other mixing device. The size of the reaction vessel (i.e., reaction zone) is chosen to give a residence time (defined as the volume slurry maintained in the vessel divided by the total volumetric feed rate) greater than about 10 minutes, such as about 30 minutes or about 1 hour. Agitation can be provided by an agitator or by a circulation loop or by both means. Reactor vessels, such as crystallizers, will typically be equipped with internal baffles arranged about the periphery of the vessel, and may be equipped with a draft tube.

The residence time of the slurry in the crystallizer is greater than 10 minutes, such as about 30 minutes or about 1 hour.

In an alternate embodiment at least a portion of the acid or all of the acid may be added within the reaction zone (e.g., crystallizer) provided that desirable product crystal characteristics are maintained.

In yet another alternate embodiment the preparation may be conducted in a batch-wise fashion. In the batch mode, at least one of the feed constituents is fully charged to the reaction zone, e.g., crystallizer, before the other feed constituents are added. For example, the crystallizer may be charged with the aqueous solution of TPBA and then the stream comprising pyridine may then be added over a period of time. Alternatively, the crystallizer may be charged with water, and both the aqueous solution of TPBA and the stream comprising pyridine may be added simultaneously or substantially simultaneously over a period time. The batch reaction time in the crystallizer is greater than about 10 minutes, such as about 30 minutes or about 1 hour. The product slurry produced in the reaction zone is reacted with a sufficient amount of any non-oxidizing acid, such as HCl, to adjust the pH of the product slurry to a value of about 8.5 to about 12, such as about 9.5 to about 10.5. The concentration of the acid is not critical, and normally concentrated acid, e.g., concentrated HCl, would be used. The acid may be added to the product slurry in the crystallizer once TPBP reaction is complete. Alternatively the product slurry may be fed from the crystallizer to a separate vessel, e.g., agitated tank, where the acid may be added. Aside from the batch reaction time, the addition of the acid, and any changes necessitated by it, such as modification of the pH, the specific mode of operation of the crystallizer is described in detail in the JP 1074 Application.

EXAMPLES

All experiments were performed in a 1-liter cylindrical vessel, which has a height to diameter ratio of contained slurry of approximately 1.0. The vessel had four baffles with standoffs, and was equipped with a six-blade turbine agitator. There were two feed points located at the same level as the turbine. The feeds were located on the outside tip of the agitator blades, and 180 degrees apart. Pyridine was added through one feed point, and TPBA solution was added through the second feed point. Product was removed by overflow from the top of the vessel to maintain a relatively constant volume in the vessel.

The slurry product was characterized in the following ways to evaluate the quality of the product:

Photomicrographs were taken to determine particle size and shape.

Cake moisture to determine the amount of water in the cake after filtration.

Amount of solid product recovered.

Cake moisture was determined by weighing the wet filter cake to get the weight of water plus solids, followed by drying in a vacuum oven and re-weighing to obtain the weight of dry solids. Cake moisture was calculated as follows:

Cake Moisture=(Weight of wet cake−Weight of dry solids)/Weight of dry solids.

Recovery was determined by measuring the amount of dry solid obtained from a given volume of slurry.

Comparative Example 1

Crystallization without Neutralization

In this experiment an aqueous solution of the sodium form of TPBA (containing 4 wt % triphenylboron) was fed at a rate of 8.3 cc/min, and undiluted pyridine was fed at 7.3 cc/hr. This corresponds to a near stoichiometric mixture, and the residence time was about 1 hr. The temperature of the crystallizer was controlled at 40° C. After 4 hours of operation, a sample of the slurry was characterized. The product obtained consisted of round particles, as shown in FIG. 1. Additional data is shown in Table 1 under the heading Example 1.

Example 2

Crystallization Followed by Neutralization to pH=7.0

This is a continuation of Example 1, where the crystallizer was run for an additional hour to collect slurry for neutralization. The slurry contained TPBP particles and dissolved TPBP. Concentrated HCl was added to the slurry with mixing to neutralize the caustic (NaOH), while the pH was measured with a standard pH meter. When the pH reached a value of 8.5, noticeable flocculation of the solids occurred. Additional acid was added to reduce the slurry pH to 7.0. The slurry was then characterized. A micrograph of the solids showed that they were transformed to a granular shape, as shown in FIG. 2. Additional data for this Example are given in Table 1. The addition of the HCl increased the TPBP recovery by 12.8%, but the cake moisture increased by three-fold.

Comparative Example

Crystallization without Neutralization

In this experiment an aqueous solution of the sodium form of TPBA (containing 4 wt % triphenylboron) was fed at a rate of 8.3 cc/min, and undiluted pyridine was fed at 7.0 cc/hr. This corresponds to a near stoichiometric mixture, and the residence time was about 1 hr. The temperature of the crystallizer was controlled at 40° C. After 4 hours of operation, a sample of the slurry was characterized. The product obtained consisted of round particles, as shown in FIG. 3. Additional data is shown in Table 1.

Example 4

Crystallization Followed by Neutralization to pH=10.0

This is a continuation of Example 3, where the crystallizer was run for an additional hour to collect slurry for neutralization. The slurry contained TPBP particles and dissolved TPBP. Concentrated HCl was added to the slurry with mixing to neutralize the caustic, while the pH was measured with a standard pH meter. The acid was added until the pH reached 10.0. No flocculation of the particles was observed. The slurry was then characterized. A micrograph of the solids showed that they were spherical in shape, as shown in FIG. 4. Additional data for this Example are given in Table 1. The addition of the HCl increased the TPBP recovery by 11.5%, and there was a reduction in the cake moisture.

These examples show that by adjusting the slurry pH to a value of 10, there is a significant increase in product recovery, and desirable particle characteristics are retained. Reducing the pH below a value of 8.5 gives increased recovery, but is accompanied by significant deterioration of the particles.

TABLE 1

|  | Example 1 | Example 2 | Example 3 | Example 4 |
|---|---|---|---|---|
| Crystal Shape | Spheres | Granules | Spheres | Spheres |
| Cake Moisture (g W/g S) | 0.20 | 0.60 | 0.50 | 0.35 |
| Recovery (gm TPBP/liter) | 47 | 53 | 40 | 44.6 |

All documents described or mentioned herein are incorporated by reference herein in their entirety, including any priority documents and/or testing procedures to the extent they are not inconsistent with this specification. As is apparent from the foregoing general description and the specific embodiments, while forms of the disclosure have been illustrated and described, various modifications can be made without departing from the spirit and scope thereof. Accordingly, it is not intended that the invention be limited thereby.

The invention claimed is:

1. A process for producing triphenylboron-pyridine (TPBP) comprising generally spherical solid particles which comprises:
   (A) providing a product slurry comprising solid TPBP particles in an aqueous mother liquor in a vigorously agitated reaction zone;
   (B) separately feeding into said vigorously agitated reaction zone (i) a stream of pyridine and (ii) a stream comprising a solution of an alkali hydroxide adduct of triphenylboron (TPBA), whereby the total concentration of TPBA in the combined feed streams is in the range of from about 1 wt % to about 6 wt %, to form additional TPBP in the product slurry;
   (C) adding to the product slurry a sufficient amount of acid to adjust pH of the product slurry to a value of about 8.5 to about 12.0; and
   (D) removing a product stream from said reaction zone at such a rate that the volume of said product slurry in the reaction zone remains substantially constant, and the concentration of solid TPBP in the product slurry is maintained at a value of less than about 8 wt %.

2. The process of claim 1, wherein the amount of the acid added is sufficient to adjust the pH of the product slurry to a value of about 9 to about 12.

3. The process of claim 1, wherein the amount of the acid added is sufficient to adjust the pH of the product slurry to a value of about 9.5 to about 11.

4. The process of claim 1, wherein the amount of the acid added is sufficient to adjust the pH of the product slurry to a value of about 9.5 to about 10.5.

5. The process of claim 1, wherein the acid is a non-oxidizing acid.

6. The process of claim 1, wherein the acid is hydrochloric acid, sulfuric acid, phosphoric acid, or acetic acid.

7. The process of claim 1, wherein the acid is hydrochloric acid.

8. The process of claim 1, wherein the total concentration of TPBA in the combined feed streams is in the range of from about 3 wt % to about 5 wt %.

9. The process of claim 1 in which the temperature of the product slurry of solid TPBP particles in the aqueous mother liquor in the reaction zone is maintained in the range of from about 20° C. to about 60° C.

10. The process of claim 9 in which the temperature is maintained in the range of from about 35° C. to about 45° C.

11. A process for producing triphenylboron-pyridine (TPBP) which comprises:
   (A) separately feeding into a reaction zone (i) a stream comprising pyridine and (ii) a stream comprising a solution of an alkali hydroxide adduct of triphenylboron (TPBA) to form a product slurry comprising TPBP in an aqueous mother liquor;
   (B) adding to the reaction zone a sufficient amount of acid to adjust pH of the product slurry to a value of about 8.5 to about 12.0;
   (C) removing a product stream from said reaction zone which includes the TPBP particles.

12. The process of claim 11, wherein the amount of the acid added is sufficient to adjust the pH of the product slurry to a value of about 9 to about 12.

13. The process of claim 11, wherein the amount of the acid added is sufficient to adjust the pH of the product slurry to a value of about 9.5 to about 11.

14. The process of claim 11, wherein the amount of the acid added is sufficient to adjust the pH of the product slurry to a value of about 9.5 to about 10.5.

15. The process of claim 11, wherein the acid is a non-oxidizing acid.

16. The process of claim 11, wherein the acid is hydrochloric acid, sulfuric acid, phosphoric acid, or acetic acid.

17. The process of claim 11, wherein the acid is hydrochloric acid.

18. A process of claim 1, wherein the acid is added to the reaction zone.

19. A process of claim 1, wherein the acid is added in a vessel separate from the reaction zone.

20. A process of claim 11, wherein the acid is added to the reaction zone.

21. A process of claim 11, wherein the acid is added to a vessel separate from the reaction zone.

* * * * *